United States Patent
Jiang et al.

(10) Patent No.: US 10,402,963 B2
(45) Date of Patent: Sep. 3, 2019

(54) DEFECT DETECTION ON TRANSPARENT OR TRANSLUCENT WAFERS

(71) Applicant: KLA-Tencor Corporation, Milpitas, CA (US)

(72) Inventors: Xuguang Jiang, Sunnyvale, CA (US); Yong Zhang, Cupertino, CA (US); Yiwu Ding, Danville, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 111 days.

(21) Appl. No.: 15/803,091

(22) Filed: Nov. 3, 2017

(65) Prior Publication Data
US 2019/0066284 A1    Feb. 28, 2019

Related U.S. Application Data

(60) Provisional application No. 62/549,775, filed on Aug. 24, 2014.

(51) Int. Cl.
| | |
|---|---|
| *G06K 9/00* | (2006.01) |
| *G06T 7/00* | (2017.01) |
| *G06T 7/136* | (2017.01) |
| *G06T 5/50* | (2006.01) |
| *G06T 7/55* | (2017.01) |

(52) U.S. Cl.
CPC ............ *G06T 7/001* (2013.01); *G06T 5/50* (2013.01); *G06T 7/136* (2017.01); *G06T 7/55* (2017.01); *G06T 2207/20224* (2013.01)

(58) Field of Classification Search
CPC combination set(s) only.
See application file for complete search history.

(56) References Cited

U.S. PATENT DOCUMENTS

| | | | |
|---|---|---|---|
| 5,216,481 A | 6/1993 | Minato | |
| 6,407,373 B1 * | 6/2002 | Dotan | G01N 21/9501 250/201.3 |
| 6,807,454 B2 * | 10/2004 | Wang | G05B 19/41875 700/110 |
| 7,433,031 B2 * | 10/2008 | Xu | G01N 21/21 356/237.2 |
| 7,502,102 B2 | 3/2009 | Johannesson | |

(Continued)

FOREIGN PATENT DOCUMENTS

KR    20150131114 A    11/2015

OTHER PUBLICATIONS

ISA/KR, International Search Report and Written Opinion for PCT/US2018/047620 dated Dec. 4, 2018.

*Primary Examiner* — Amir Alavi
(74) *Attorney, Agent, or Firm* — Hodgson Russ LLP

(57) ABSTRACT

Defect detection on transparent or translucent wafers can be performed on a die using references from the same die. A first calculated value based on a kernel size, such as a moving mean, is determined. A first difference is determined by subtracting the first calculated value from a pixel intensity. Candidate pixels with a first difference above a threshold are classified. A second calculated value based on a kernel size, such as a local median, is determined. A second difference is determined by subtracting the second calculated value from the pixel intensity. Pixels that include a defect are classified when the second difference is above the threshold.

19 Claims, 13 Drawing Sheets

(56) References Cited

U.S. PATENT DOCUMENTS

| | | | |
|---|---|---|---|
| 8,537,349 B2* | 9/2013 | Huet | G01R 31/2656 |
| | | | 356/237.2 |
| 8,595,666 B2* | 11/2013 | Hayakawa | G01N 21/95607 |
| | | | 716/112 |
| 8,599,379 B2* | 12/2013 | Sakai | G01N 21/9505 |
| | | | 356/237.1 |
| 9,150,758 B2* | 10/2015 | Miller | H01L 21/3212 |
| 9,881,365 B2* | 1/2018 | Tandai | G06T 7/001 |
| 2003/0094586 A1* | 5/2003 | Kurosawa | G01N 21/9501 |
| | | | 250/559.4 |
| 2008/0062422 A1 | 3/2008 | Thomas et al. | |
| 2010/0189339 A1 | 7/2010 | Amanullah et al. | |
| 2019/0066284 A1* | 2/2019 | Jiang | G06T 7/001 |

\* cited by examiner

| Channel | Area | Region | DieMode | LRA | SDA | LNT | ALGO | Intensity |
|---|---|---|---|---|---|---|---|---|
| DF | 169.85 | BASE | Primary | 21.80 | 0.00 | 0.00 | LRA | 116 |
| DF | 254.77 | BASE | Primary | 37.60 | 0.00 | 0.00 | LRA | 195 |
| BF | 42.46 | BASE | Primary | 14.61 | 0.00 | 0.00 | LRA | 597 |
| DF | 42.46 | BASE | Primary | 13.20 | 0.00 | 0.00 | LRA | 73 |
| DF | 169.85 | BASE | Primary | 27.60 | 0.00 | 0.00 | LRA | 145 |
| DF | 254.77 | BASE | Primary | 41.00 | 0.00 | 0.00 | LRA | 212 |
| DF | 169.85 | BASE | Primary | 15.40 | 0.00 | 0.00 | LRA | 83 |
| DF | 84.92 | BASE | Primary | 12.40 | 0.00 | 0.00 | LRA | 69 |

FIG. 16

DEFECT DETECTION ON TRANSPARENT OR TRANSLUCENT WAFERS

CROSS-REFERENCE TO RELATED APPLICATIONS

This application claims priority to the provisional patent application filed Aug. 24, 2017 and assigned U.S. App. No. 62/549,775, the disclosure of which is hereby incorporated by reference.

FIELD OF THE DISCLOSURE

This disclosure relates to defect detection on transparent or translucent wafers.

BACKGROUND OF THE DISCLOSURE

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

For transparent or translucent wafers, an image from certain defect detection systems can contain contributions from both the wafer and the tool parts such as the chuck under the wafer. Defect detection on transparent or translucent wafers provides unique challenges. For example, the chuck under the wafer appears during defect detection of a glass wafer. The glass wafer contains some structures or devices, which can be difficult to discern during defect detection when chuck components are also imaged. When a chuck shows up in the glass wafer image, existing defect detection tools or algorithms cannot meet defect detection sensitivity or throughput targets for semiconductor manufacturers.

In another example, a chuck pattern appears in a bright field image, while chuck surface roughness appears in a dark field image. The chuck patterns in each die are different. Thus, existing defect detection algorithms cannot provide satisfactory defect detection on those transparent or translucent wafers. For example, the algorithm may only be able to detect large defects on wafer with the smallest pixel size (e.g., 10× or 0.65 μm) with degraded inspection sensitivity.

Examples are seen in FIGS. 1-3. FIG. 1 illustrates three exemplary dies on a glass wafer with both bright field and dark field imaging. As seen in the bright field images of die 0 and die 1, the chuck is visible through the glass wafer. Surface roughness can be seen in each of the dark field images. Defects of interest (DOI) are circled in the bright field images of die 0 and die 2. FIG. 2 illustrates image subtraction of die 2 and die 0 and also image subtraction of die 2 and die 1. Noise is present in each image, which makes detection of the defects challenging. FIG. 3 shows additional image analysis of the bright field images. As seen in FIG. 3, there are one or two DOI circled in some die images. The DOI are dwarfed by the chuck components. The algorithm will provide poor defect detection performance of images such as those in FIG. 3.

Therefore, improvements to defect detection on transparent or translucent wafers are needed.

BRIEF SUMMARY OF THE DISCLOSURE

In a first embodiment, a system is provided. The system includes a controller. The controller includes a processor and an electronic data storage unit in electronic communication with the processor. The processor is configured to execute one or more software modules. The one or more software modules are configured to receive bright field images for three dies. The three dies are on a transparent or translucent wafer. Each of the bright field images includes a plurality of image rows and a plurality of image columns. The one or more software modules are configured to receive dark field images for the three dies. Each of the dark field images includes a plurality of the image rows and a plurality of the image columns. The one or more software modules are configured to determine a first calculated value for each of the image columns of the bright field images and the dark field images. The first calculated value is based on a kernel size applied along at least one of the image columns. The one or more software modules are configured to determine a first difference by subtracting the first calculated value from a pixel intensity in each pixel of the image columns; classify candidate pixels; determine a second calculated value; determine a second difference by subtracting the second calculated value from the pixel intensity; and classify the pixels that include a defect. The first difference for the candidate pixels is above a threshold. The second calculated value is based on the kernel size. The second difference is above the threshold for the pixels that include a defect. The three dies can be neighboring dies.

A bright field imaging system and/or a dark field imaging system may be in electronic communication with the controller.

The first calculated value may be a moving mean. The second calculated value may be a local median.

The second calculated value may be of each of the candidate pixels. The second difference may be from each of the candidate pixels.

In a second embodiment, a method is provided. The method includes receiving, at a controller, bright field images for three dies. The three dies are on a transparent or translucent wafer. Each of the bright field images includes a plurality of image rows and a plurality of image columns. Dark field images for the three dies are received at the controller. Each of the dark field images includes a plurality of the image rows and a plurality of the image columns. A first calculated value is determined, using the controller, for each of the image columns of the bright field images and the dark field images. The first calculated value is based on a kernel size applied along at least one of the image columns. A first difference is determined, using the controller, by subtracting the first calculated value from a pixel intensity in each pixel of the image columns. Candidate pixels are classified using the controller. The first difference for the candidate pixels is above a threshold. A second calculated value is determined using the controller. The second calculated value is based on the kernel size. A second difference is determined, using the controller, by subtracting the second calculated value from the pixel intensity. The pixels that include a defect are classified using the controller. The second difference is above the threshold for the pixels that include a defect. The three dies may be neighboring dies.

The first calculated value may be a moving mean. The second calculated value may be a local median.

One of the first calculated value and the second calculated value can be a fast Fourier transform with a low pass filter. One of the first calculated value and the second calculated value can be a convolution with a Gaussian kernel.

The second calculated value can be of each of the candidate pixels. The second difference may be from each of the candidate pixels.

In an instance, the pixel intensity can be an average of three neighboring pixels in a same image column of the same die. The second calculated value can be an average of the candidate pixels and two neighboring pixels in the same image column of the same die. The second difference can be based on the average of the candidate pixels.

The first calculated value can be determined for each of the bright field images and each of the dark field images.

The first calculated value and the second calculated value can be determined based on fused images of each of the bright field images and a corresponding one of each of the dark field images of a same die. Each of the bright field images and the corresponding one of each of the dark field images can be fused to form the fused images.

In an instance, the second calculated value is a local median. The second calculated value and the second difference can be determined based on both the bright field images and the dark field images. The threshold can include a bright field threshold and a dark field threshold.

In another instance, the second calculated value is a local median. The threshold can be for the fused images. The classifying can include taking the square root of the product of a first value and a second value to form a third value and comparing the third value to the threshold. The first value can be the pixel intensity of the bright field image minus the local median of the bright field image. The second value can be the pixel intensity of the dark field image minus the local median of the dark field image.

DESCRIPTION OF THE DRAWINGS

For a fuller understanding of the nature and objects of the disclosure, reference should be made to the following detailed description taken in conjunction with the accompanying drawings, in which:

FIG. 16 is an exemplary table of defect attributes that can be used in the LRA.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The inspection method, system, and algorithm disclosed herein can be used for defect detection on transparent and translucent wafers, such as glass wafers, sapphire wafers, or wafers made of other materials. This inspection algorithm detects defects on each die using references only from the same die. Thus, the inspection algorithm is not affected by differences in the images between neighbor dies. The inspection algorithm also can remove a chuck pattern in each die using local reference pixels. Thus, the inspection algorithm can be used when a die image contains patterns. The inspection algorithm also can include a setup step for inspection algorithm parameter evaluation and a detection step for wafer inspection.

Figure 1:
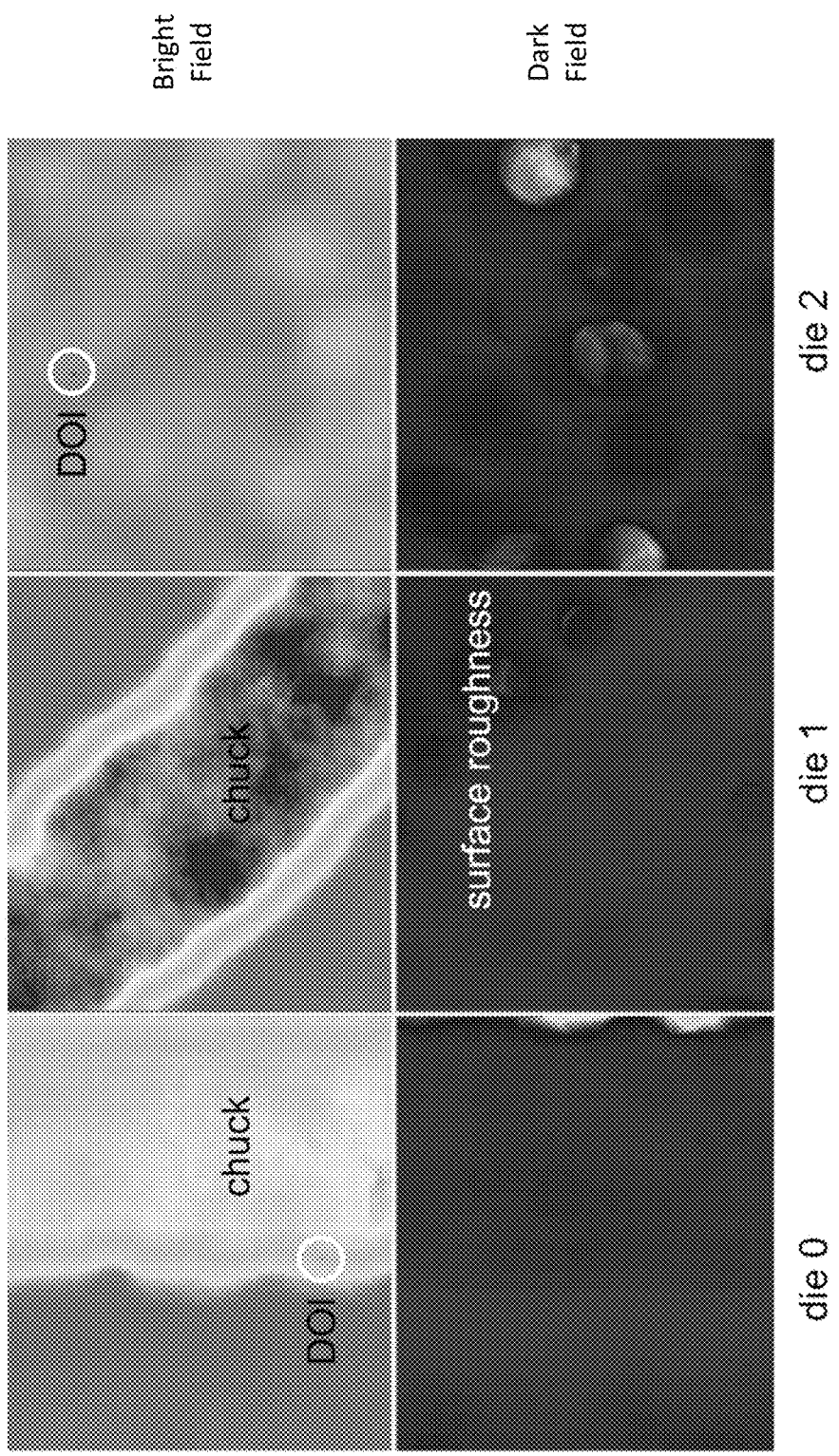
FIG. 1 illustrates three exemplary dies with both bright field and dark field imaging of a glass wafer.
Figure 2:
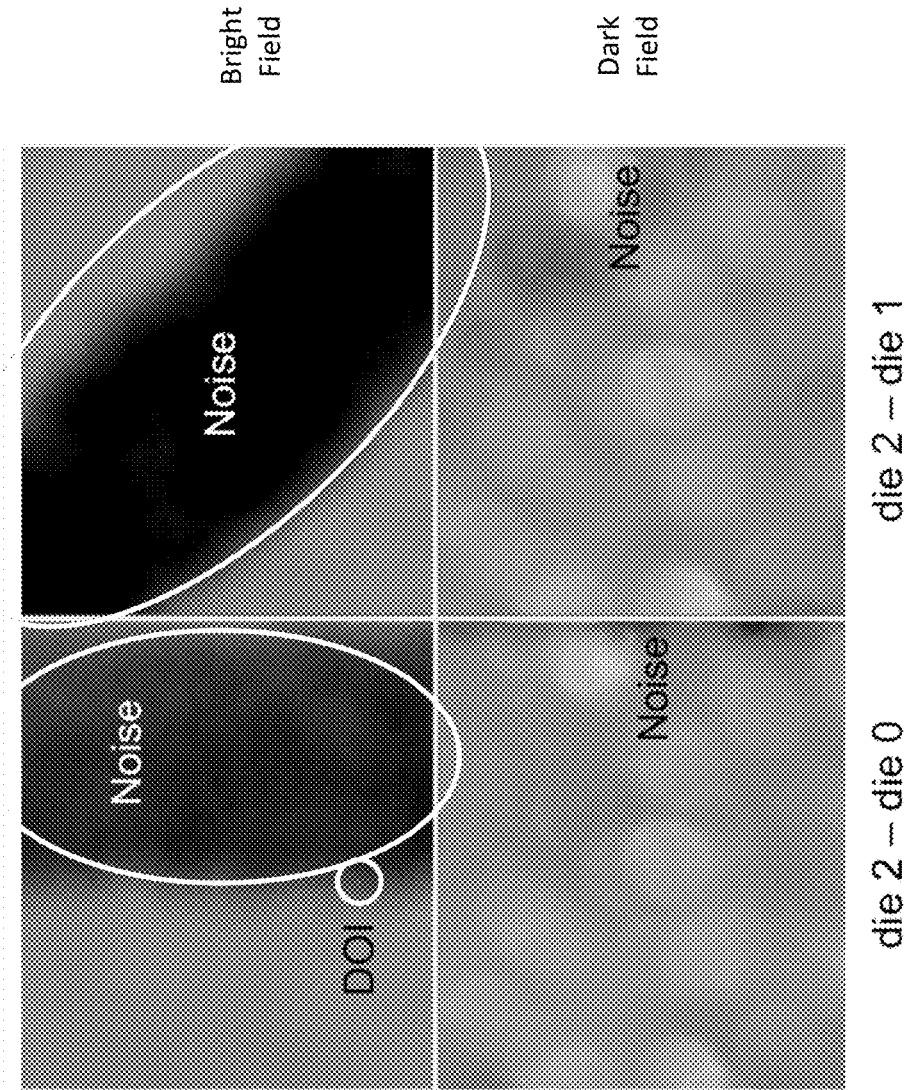
FIG. 2 illustrates image subtraction using the dies of FIG. 1.
Figure 3:
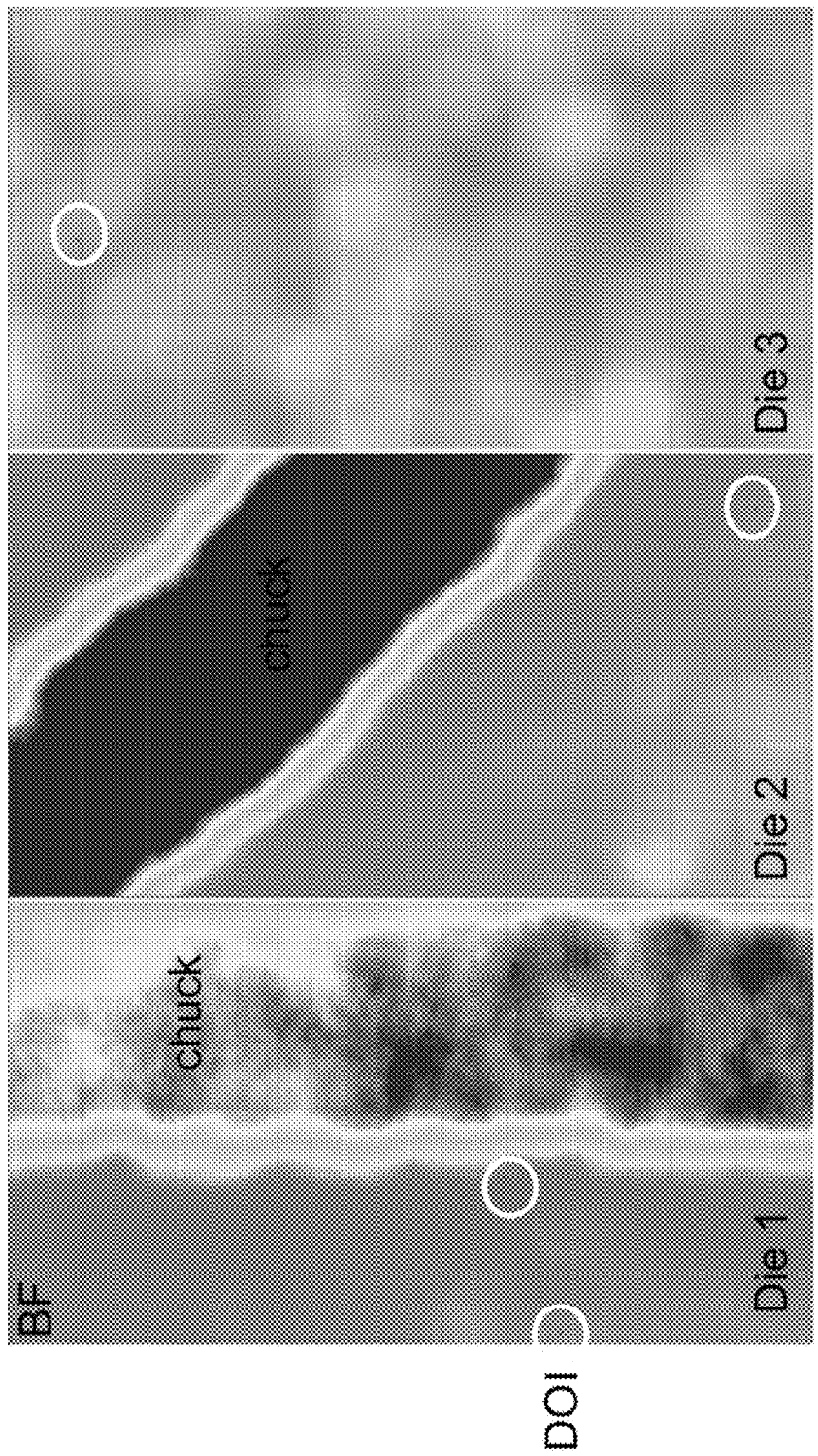
FIG. 3 provides additional image analysis of the bright field images of a glass wafer.
Figure 4:
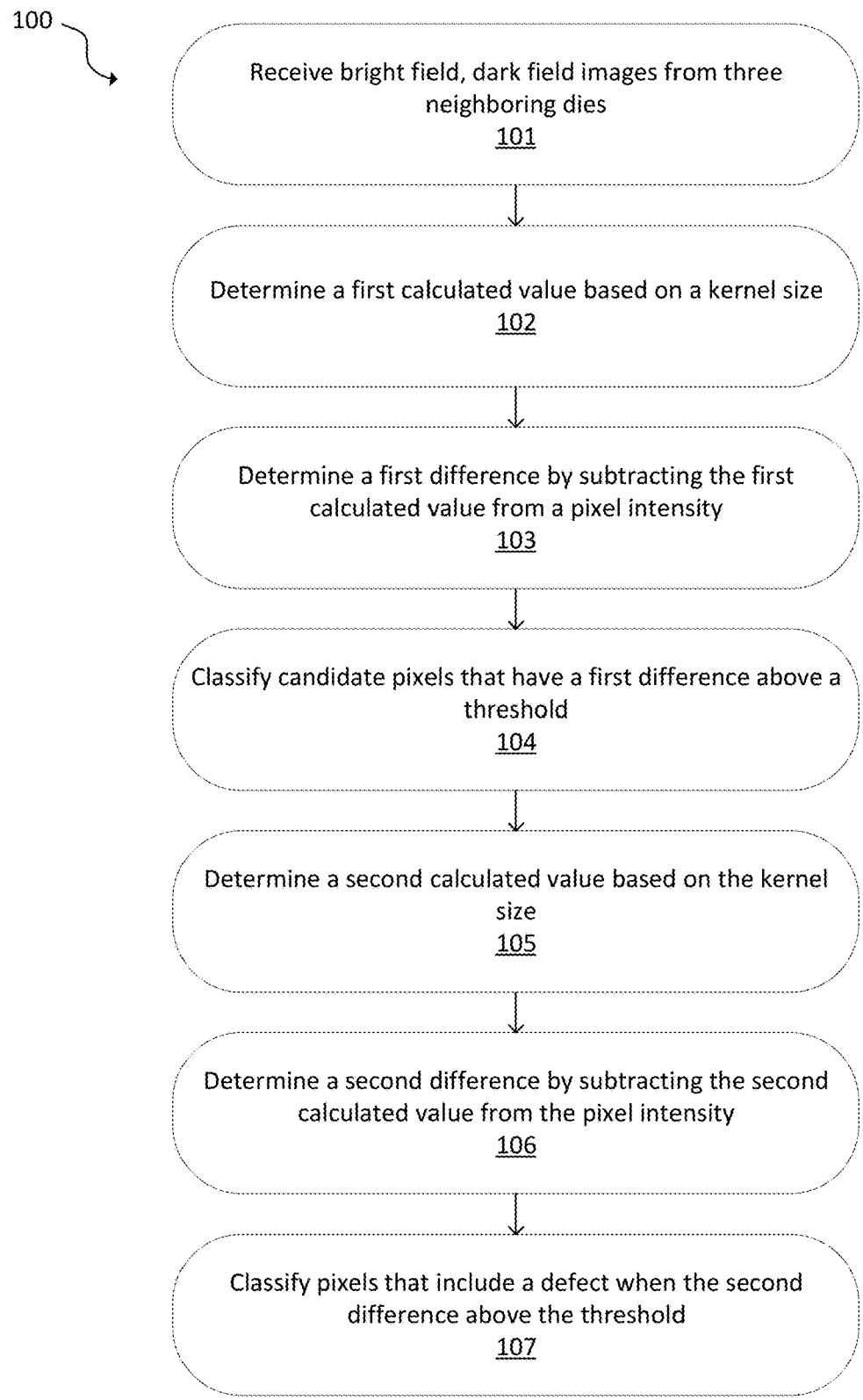
FIG. 4 is a flowchart of an embodiment of a method in accordance with the present disclosure.

FIG. 4 is a flowchart of an embodiment of a method 100. Each of the steps 101-107 in method 100 may be performed using a controller. As seen in this embodiment, a reference can be calculated using local pixels from a single die. The method 100 has a two-step detection method. In an instance, the method 100 uses a mean for fast candidate selection and a median for accurate defect detection, though other techniques are possible. The mean may be a moving mean. The method 100 enables defect detection with high sensitivity at high speed relative to existing techniques. The method 100 also improves results for transparent or translucent wafers.

Bright field and dark field channel images from three neighbor dies can be used in the method 100. The method 100 can perform defect detection independently on each die and each channel. Instead of using a neighbor die as reference, neighbor pixels on the same die are used as a reference for defect detection. If there is no image fusion, then the detection on bright and dark channels may be performed independently. A defect is classified if either channel detects it.

Thus, for each column in the bright field and dark field images, a reference can be calculated using neighbor pixels. A difference can be calculated by subtracting the reference from the original. Defects can be detected if the absolute value of the difference is greater than a threshold. This may occur in two stages. First, candidate detection that compares every pixel with local neighbor mean or other value. Second, defect detection that compares a candidate pixel with local neighbor median or other value.

At 101, bright field and dark field images for three dies are received at a controller. The three dies are on a transparent or translucent wafer, such as a glass wafer. Each of the bright field images and dark field images is two dimensional and includes a plurality of image rows and image columns. While three dies are illustrated, a single die, two dies, or more than three dies also can be used. The dies, such as the three dies referred to in this embodiment, can be neighboring dies. By neighboring, it is meant that the dies are adjacent to one another on the wafer.

Figures 9, 10:
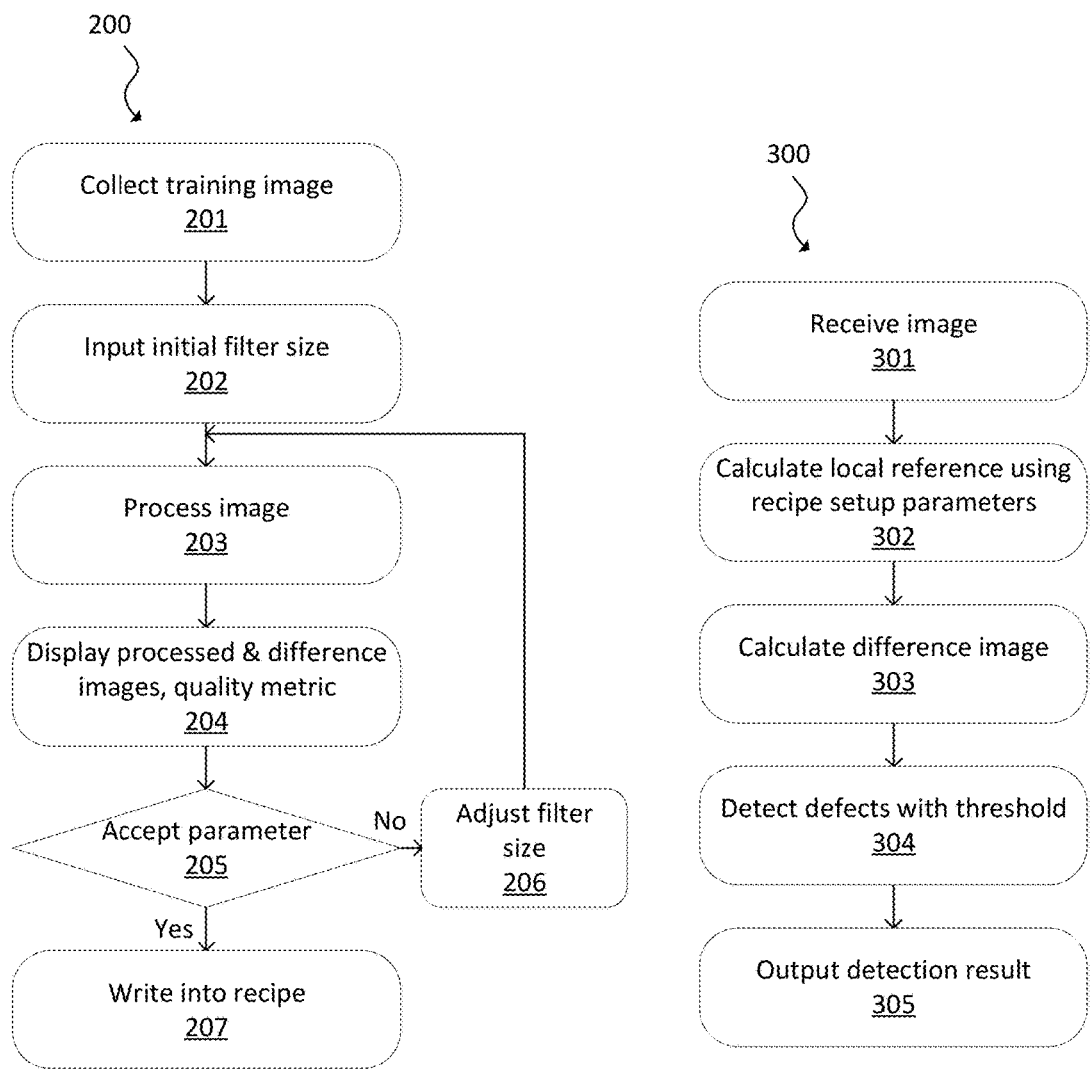
FIG. 9 illustrates a flowchart of another embodiment of the method in accordance with the present disclosure.
FIG. 10 illustrates a flowchart of yet another embodiment of the method in accordance with the present disclosure.

At 102, a first calculated value is determined for each pixel of the bright field images and the dark field images. The first calculated value is based on a kernel size applied along at least one of the image columns. In an instance, the kernel size is applied along each of the image columns. The kernel size can vary. The value may be obtained from the setup step, as seen in FIG. 9. For example, larger kernel sizes may be needed to detect larger defects.

At 103, at least one first difference is determined by subtracting the first calculated value from a pixel intensity in each pixel of the image columns. The first difference may be determined for each pixel in the image columns.

Candidate pixels are classified at 104. The first difference for any candidate pixels are above a threshold. Thus, if the first difference is greater than the threshold, the pixel is marked as a candidate pixel. The threshold can be selected by a user or using other techniques. The threshold can help determine whether pixels are real defects or noise. The threshold can be tuned or otherwise adjusted.

At 105, a second calculated value is determined. The second calculated value is based on the kernel size. The second calculated value may be determined for each candidate pixel in the image columns.

At 106, a second difference is determined by subtracting the second calculated value from the pixel intensity.

The pixels that include a defect are classified at 107. The second difference is above the threshold for the pixels that include a defect. Thus, if the second difference is greater than the threshold, the pixel is marked as defective. A report or summary of defective pixels can be generated.

In an instance, the first calculated value is a moving mean and the second calculated value is a local median. The mean may be calculated quickly and can provide fast candidate selection. The local median may be slower to calculate than the mean, but may provide more accurate defect detection.

In another instance, one of the first calculated value and the second calculated value is a fast Fourier transform with a low pass filter.

In yet another instance, one of the first calculated value and the second calculated value is a convolution with a Gaussian kernel.

The pixel intensity can be of each pixel. The second calculated value can be of each of the candidate pixels. The second difference can be from each of the candidate pixels.

In another instance, the pixel intensity can be an average of three neighboring pixels in the same image column of the same die. The second calculated value can be an average of the candidate pixels and its two neighboring pixels in the same image column of the same die. Using an average of three corresponding pixels can further suppress nuisance events.

The first calculated value can be determined for each of the bright field images and each of the dark field images.

The first and second calculated values also can be determined based on fused images of each of the bright field images and a corresponding one of each of the dark field images of the same die. Each of the bright field images and the corresponding one of each of the dark field images can be fused to form the fused images.

In an instance, the second calculated value is a local median. The second calculated value and the second difference are determined based on both the bright field images and the dark field images. The threshold includes a bright field threshold and a dark field threshold. A pixel may be defective if bright field pixel intensity minus the bright field median is greater than a bright field threshold and the dark field pixel intensity minus the dark field median is greater than a dark field threshold.

In another instance, the second calculated value is a local median. The threshold is for the fused images. The classifying includes taking the square root of the product of a first value and a second value to form a third value and comparing the third value to the threshold, which may be a threshold for fusion of the bright field and dark field channel images. The first value is the pixel intensity of the bright field image minus the local median of the bright field image. The second value is the pixel intensity of the dark field image minus the local median of the dark field image.

Figure 5:
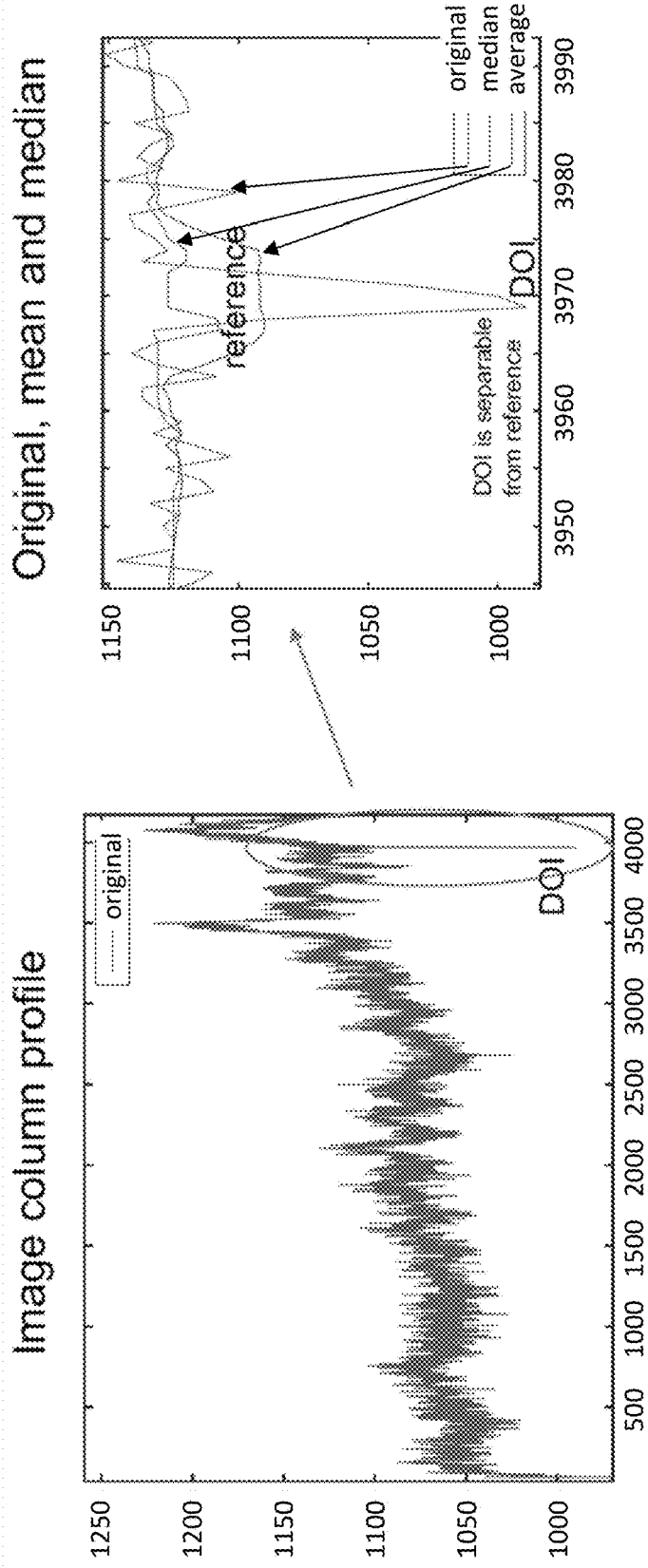
FIG. 5 illustrates a bright field image for a single image column.

FIG. 5 illustrates a bright field image for a single image column, including both a chart of the image column profile and a zoomed section around the DOI with the original intensity, mean, and median. A DOI is marked in FIG. 5. As shown on the right side image in FIG. 5, the DOI is clearly separable from the mean or median references. Thus, the neighbor pixel average and median can be acceptable references for defect detection.

Figure 6:
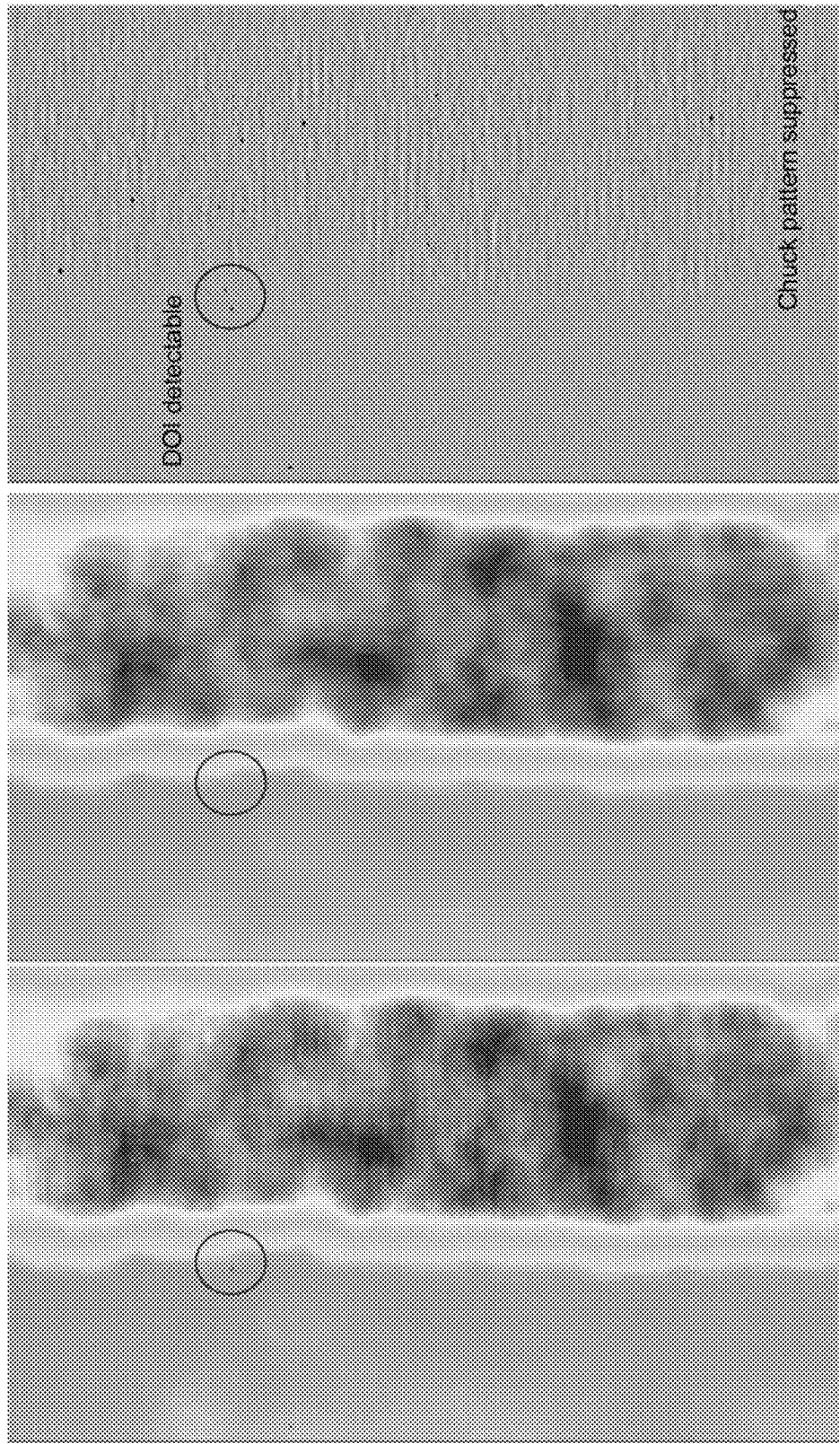
FIG. 6 illustrates an exemplary bright field image, exemplary median image, and exemplary difference image in accordance with the present disclosure.

FIG. 6 illustrates an exemplary bright field image, exemplary median image, and exemplary difference image. The difference image can be formed using, for example, the method 100. Using the embodiments disclosed herein, the DOI is detectable and the chuck pattern is suppressed. As seen in the difference image, defects can appear as dark dots.

Figure 7:
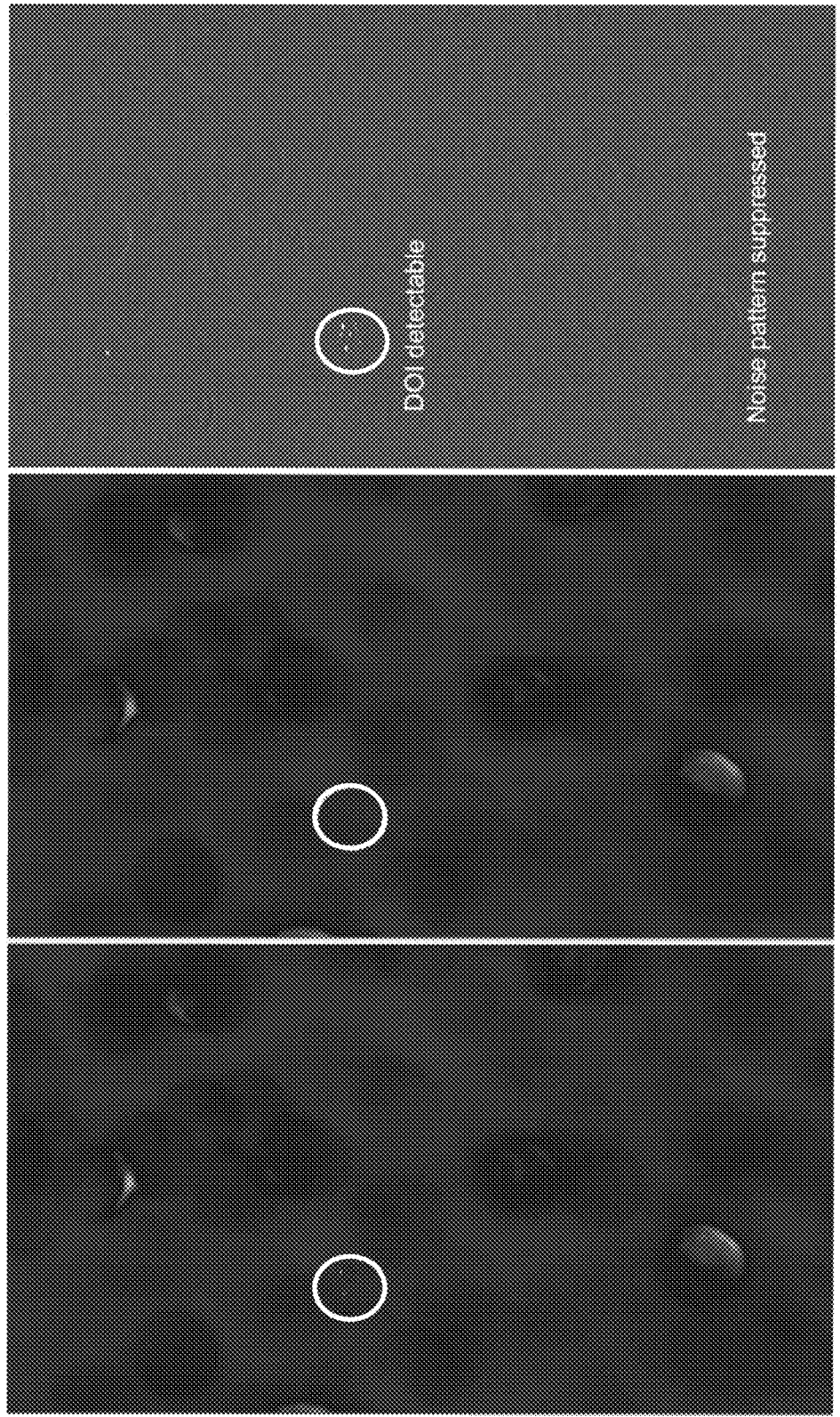
FIG. 7 illustrates an exemplary dark field image, exemplary median image, and exemplary difference image in accordance with the present disclosure.

FIG. 7 illustrates an exemplary dark field image, exemplary median image, and exemplary difference image. Using the embodiments disclosed herein, the DOI is detectable and the noise pattern is suppressed. As seen in the difference image, defects can appear as bright dots.

Figure 8:
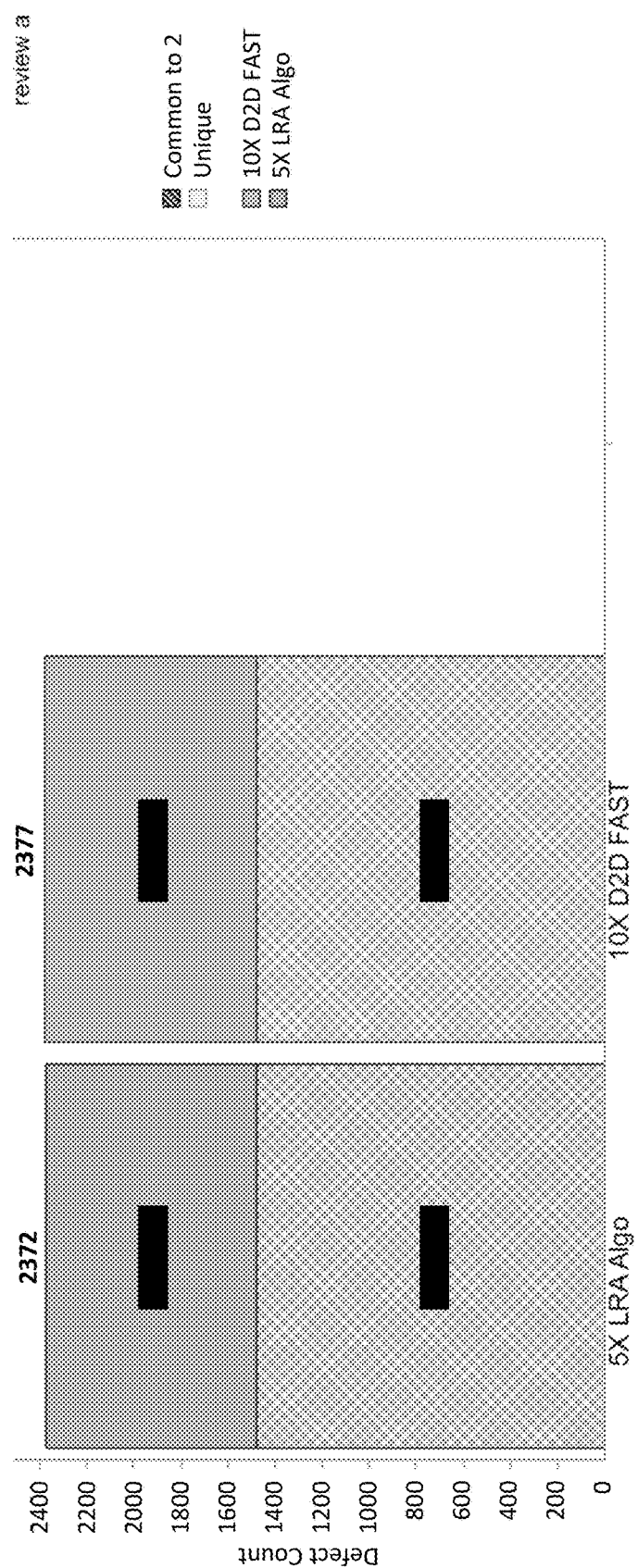
FIG. 8 illustrates a Pareto of the evaluation of a local reference algorithm (LRA) and the traditional inspection algorithm.

FIG. 8 illustrates a Pareto of the evaluation of a local reference algorithm (LRA) with a cursor pixel size (referred as 5×) and previous inspection technique with a better and finer pixel size (referred as 10×). LRA, which can include the embodiments disclosed herein, is used for defect detection. With the cursor pixel size, LRA is performed with 2.5 times faster wafer scan speed. Total defect counts are comparable. 62% of the defects are common defects. Nearly all new defects found using the technique disclosed herein are real defects.

FIGS. 9 and 10 illustrate flowcharts of other embodiments of the method. In method 200 seen in FIG. 9, which can be referred to as a setup method, training images are collected at 201. An initial filter size (e.g., a kernel size) is inputted at 202, such as by a user into a user interface. The image is processed at 203, such as by an algorithm on a controller. The processed and difference images and quality metric are displayed at 204. Then a determination is made at 205, such as by a user, whether to accept the parameter. If yes, the parameters are written into a recipe at 207. If no, the filter size is adjusted at 206 and some steps are repeated. This can enable the filter size or other parameters to be tuned.

Figure 12:
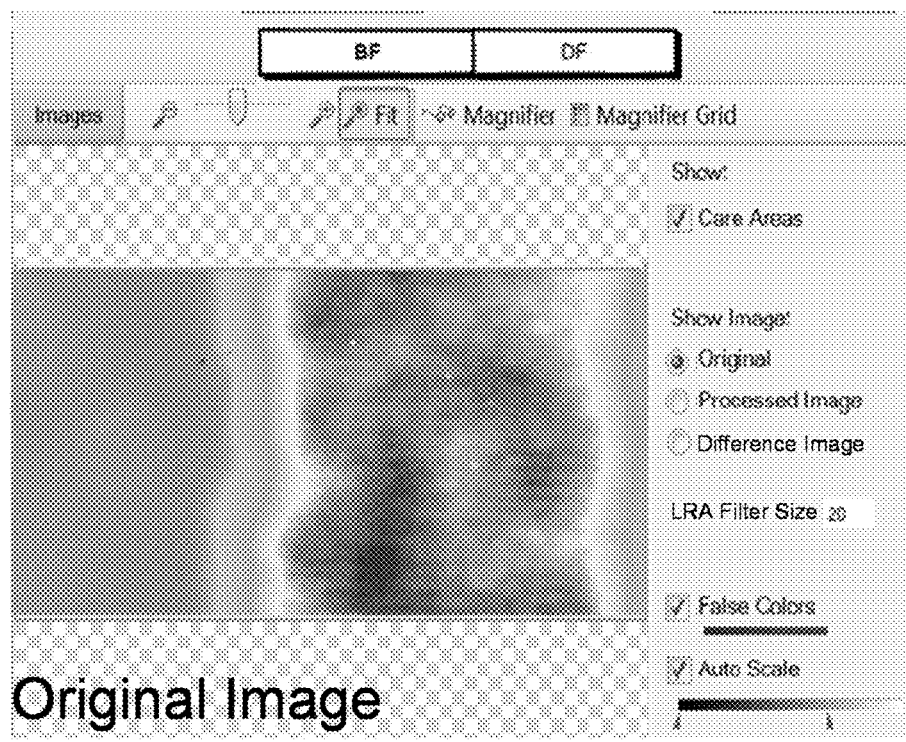
FIG. 12 is an image of an embodiment of a user interface with an original image in accordance with the present disclosure.
Figure 13:
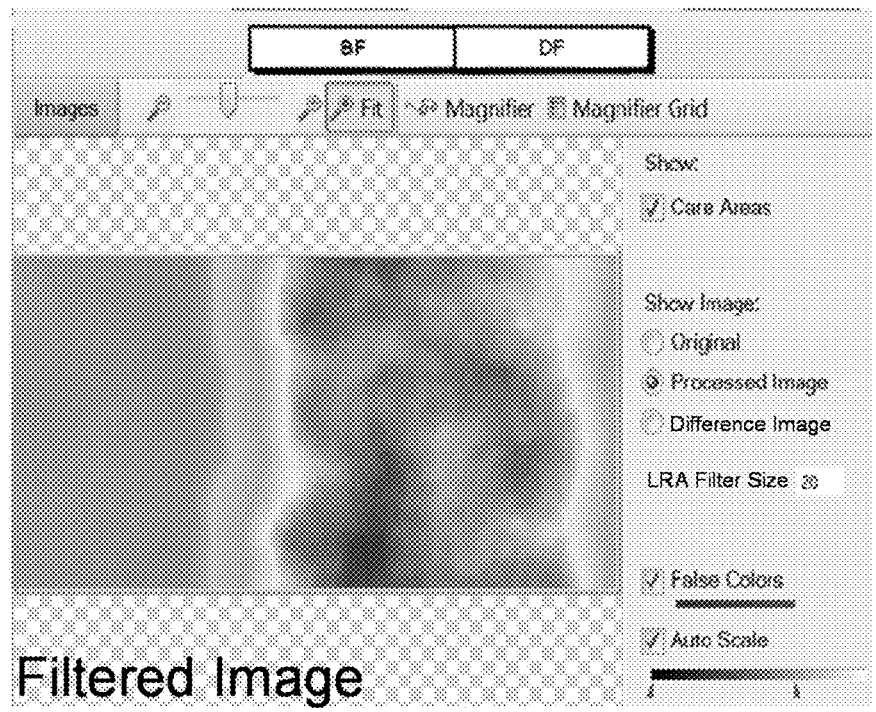
FIG. 13 is an image of an embodiment of a user interface with a filtered image in accordance with the present disclosure.
Figure 14:
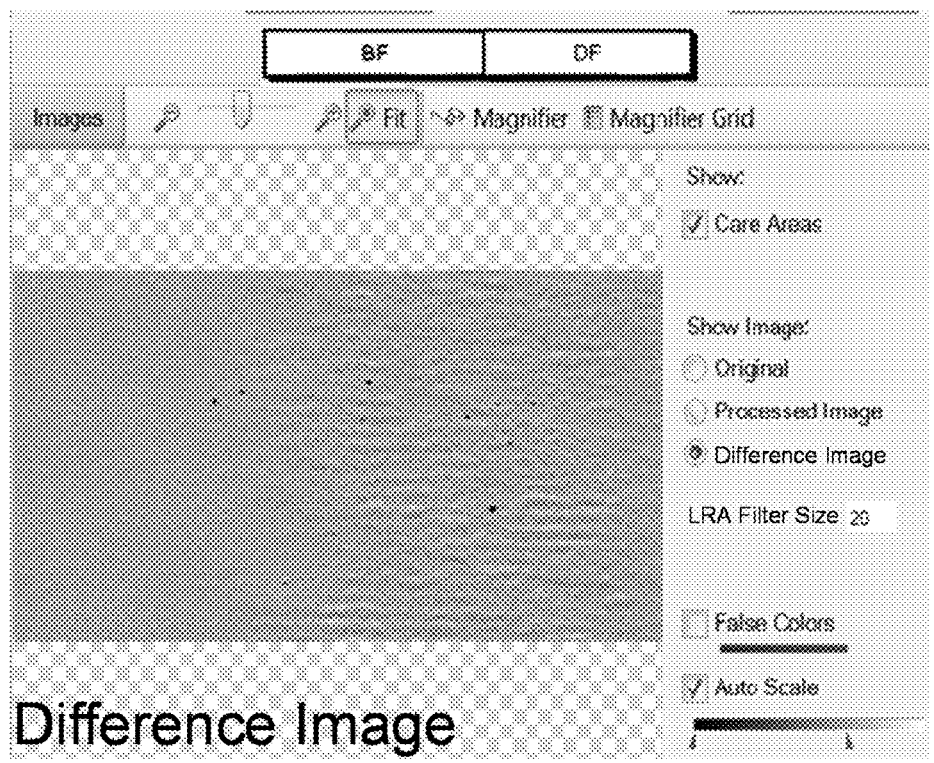
FIG. 14 is an image of an embodiment of a user interface with a difference image in accordance with the present disclosure.
Figure 15:
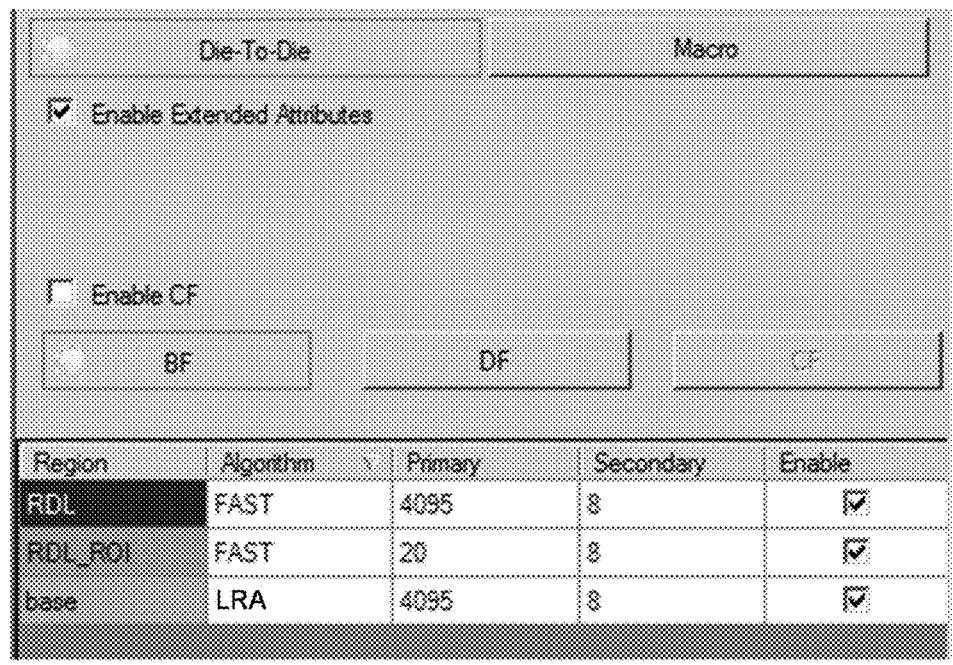
FIG. 15 is an image of an embodiment of a user interface for editing a recipe in accordance with the present disclosure.

In an algorithmic implementation, the parameters of the method can be evaluated during the setup step using the filter size that is selected. A user can grab an image around a tool chuck structure or other parts that may need to be suppressed. The user can input a filter size. The algorithm can process the images and output both reference and difference images. The user can adjust the filter size to provide a best result. The parameter can be filled into a recipe, such as in an XML file. The user can tune other recipe parameters to provide improved defect detection results. FIG. 12 is an example of a user interface with an original image, FIG. 13 is an example of a user interface with a filtered image, and FIG. 14 is an example of a user interface with a difference image. The image in FIG. 13 removes some components, spots, or marks of the image in FIG. 12. FIG. 15 is an example of a user interface for editing a recipe, which shows the LRA. Filter size and other algorithm parameters can be shown in the recipe.

Method 300 in FIG. 10 can be referred to as an inspection step. Some or all of the steps from the method 100 in FIG. 4 may be performed in the method 300. At 301, an image is received. A local reference is calculated using recipe parameters, such as those from the method 200, at 302. A difference image is calculated at 303. Defects are detected with a threshold at 304 and detection results are outputted at 305. FIG. 16 is an exemplary table of defect attributes that can be used in the LRA. FIG. 16 may be part of a review user interface. A user can tune the LRA recipe parameters for improved defect detection results based on the LRA attribute.

Figure 11:
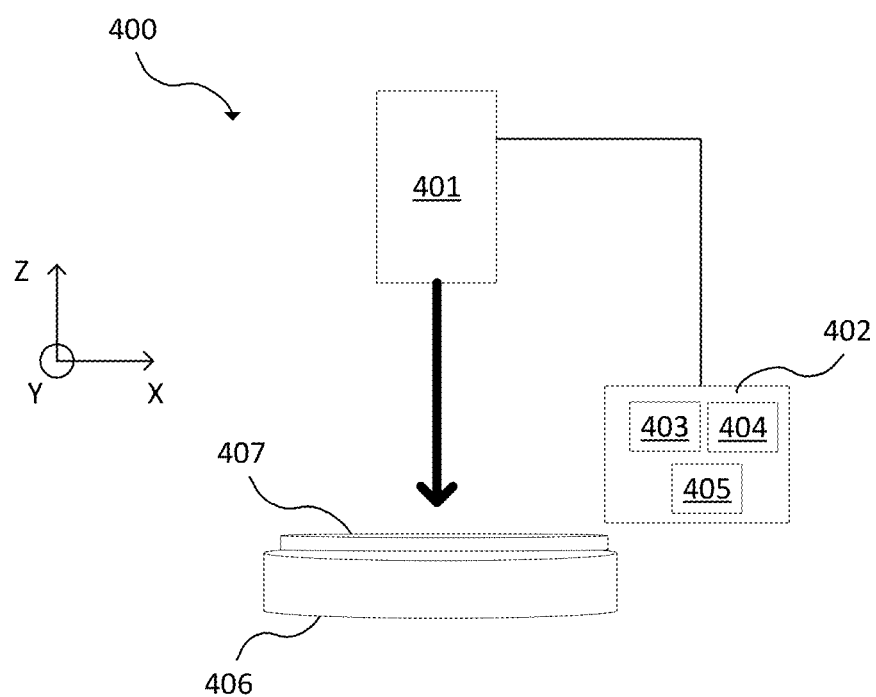
FIG. 11 is a block diagram of an embodiment of a system in accordance with the present disclosure.

FIG. 11 is a block diagram of an embodiment of a system 400. The system 400 includes a chuck 406 configured to hold a wafer 407, reticle, or other workpiece. The chuck 406 may be configured to move or rotate in one, two, or three axes. The chuck 406 also may be configured to spin, such as around the Z-axis.

The system 400 also includes a measurement system 401 configured to measure a surface of the wafer 407, reticle, or other workpiece. The measurement system 401 may produce a beam of light, a beam of electrons, broad band plasma, or may use other techniques to measure a surface of the wafer 407. In one example, the measurement system 401 includes a laser. The measurement system 401 can provide images of dies on the wafer 407 or can provide information used to form images of dies on the wafer 407.

In an instance, the measurement system 401 can produce a beam of light and includes both a bright field channel and a dark field channel. This can provide both bright field images and dark field images of the wafer 407. In an instance, the measurement system 401 includes a bright field imaging system and a dark field imaging system.

The system 400 communicates with a controller 402. For example, the controller 402 can communicate with the measurement system 401 or other components of the system 400. The controller 402 can include a processor 403, an electronic data storage unit 404 in electronic communication with the processor 403, and a communication port 405 in electronic communication with the processor 403. It is to be appreciated that the controller 402 may be implemented in practice by any combination of hardware, software, and firmware. Also, its functions as described herein may be performed by one unit, or divided up among different components, each of which may be implemented in turn by any combination of hardware, software and firmware. Program code or instructions for the controller 402 to implement various methods and functions may be stored in controller readable storage media, such as a memory in the electronic data storage unit 404, within the controller 402, external to the controller 402, or combinations thereof.

The controller 402 can include one or more processors 403 and one or more electronic data storage units 404. Each processor 403 may be in electronic communication with one or more of the electronic data storage units 404. In an embodiment, the one or more processors 403 are communicatively coupled. In this regard, the one or more processors 403 may receive readings received at the measurement system 401 and store the reading in the electronic data storage unit 404 of the controller 402. The controller 402 may be part of the system itself or may be separate from the system (e.g., a standalone control unit or in a centralized quality control unit).

In an instance, the processor includes software modules that are configured to, for example, perform some or all of the steps of method 100, method 200, or method 300.

The controller 402, other system(s), or other subsystem(s) described herein may take various forms, including a personal computer system, image computer, mainframe computer system, workstation, network appliance, internet appliance, or other device. In general, the term "controller" may be broadly defined to encompass any device having one or more processors that executes instructions from a memory medium. The subsystem(s) or system(s) may also include any suitable processor known in the art, such as a parallel processor. In addition, the subsystem(s) or system(s) may include a platform with high speed processing and software, either as a standalone or a networked tool.

The controller 402 may be coupled to the components of the system 400 in any suitable manner (e.g., via one or more transmission media, which may include wired and/or wireless transmission media) such that the controller 402 can receive the output generated by the system 400, such as output from the measurement system 401. The controller 402 may be configured to perform a number of functions using the output. For instance, the controller 402 may be configured to detect defects on the wafer 407. In another example, the controller 402 may be configured to send the output to an electronic data storage unit 404 or another storage medium without reviewing the output. The controller 402 may be further configured as described herein.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The system 400 may be part of a defect review system, an inspection system, a metrology system, or some other type of system. Thus, the embodiments disclosed herein describe some configurations that can be tailored in a number of manners for systems having different capabilities that are more or less suitable for different applications.

The controller 402 may be in electronic communication with the measurement system 401 or other components of the system 400. The controller 402 may be configured according to any of the embodiments described herein. The controller 402 also may be configured to perform other functions or additional steps using the output of the measurement system 401 or using images or data from other sources.

An additional embodiment relates to a non-transitory computer-readable medium storing program instructions executable on a controller for performing a computer-implemented method defocus detection, as disclosed herein. In particular, as shown in FIG. 11, the controller 402 can include a memory in the electronic data storage unit 404 or other electronic data storage medium with non-transitory computer-readable medium that includes program instructions executable on the controller 402. The computer-implemented method may include any step(s) of any method(s) described herein. For example, the controller 402 may be programmed to perform some or all of the steps of method 100, method 200, or method 300. The memory in the electronic data storage unit 404 or other electronic data storage medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

In another embodiment, the controller 402 may be communicatively coupled to any of the various components or sub-systems of system 400 in any manner known in the art. Moreover, the controller 402 may be configured to receive and/or acquire data or information from other systems (e.g., inspection results from an inspection system such as a review tool, a remote database including design data and the like) by a transmission medium that may include wired and/or wireless portions. In this manner, the transmission medium may serve as a data link between the controller 402 and other subsystems of the system 400 or systems external to system 400.

In some embodiments, various steps, functions, and/or operations of system 400 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape and the like. A carrier medium may include a transmission medium such as a wire, cable, or wireless transmission link. For instance, the various steps described throughout the present disclosure may be carried out by a single controller 402 (or computer system) or, alternatively, multiple controllers 402 (or multiple computer systems). Moreover, different sub-systems of the system 400 may include one or more computing or logic systems. Therefore, the above description should not be interpreted as a limitation on the present disclosure but merely an illustration.

Controller 402 may be configured to perform a number of functions using the output of the detectors. For instance, the controller 402 may be configured to detect defects on the wafer 407 using the output of the measurement system 401. Detecting the defects on the wafer 407 may be performed by the controller 402 by applying some defect detection algorithm and/or method to the output generated by the system 400. The defect detection algorithm and/or method may include those disclosed herein or any suitable algorithm and/or method known in the art. For example, the controller 402 may compare the output of the detectors to a threshold. Any output having values above the threshold may be identified as a potential defect while any output having values below the threshold may not be identified as a potential defect. In another example, the controller 402 may be configured to send the output of the system 400 to a storage medium without performing defect detection on the output. The controller 402 of the system may be further configured as described herein.

Each of the steps of the method may be performed as described herein. The methods also may include any other step(s) that can be performed by the controller and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. A system comprising:
a controller including a processor and an electronic data storage unit in electronic communication with the processor, wherein the processor is configured to execute one or more software modules, and wherein the one or more software modules are configured to:
receive bright field images for three dies, wherein the three dies are on a transparent or translucent wafer, and wherein each of the bright field images includes a plurality of image rows and a plurality of image columns;
receive dark field images for the three dies, wherein each of the dark field images includes a plurality of the image rows and a plurality of the image columns;
determine a first calculated value for each of the image columns of the bright field images and the dark field images, wherein the first calculated value is based on a kernel size applied along at least one of the image columns;
determine a first difference by subtracting the first calculated value from a pixel intensity in each pixel of the image columns;
classify candidate pixels, wherein the first difference for the candidate pixels is above a threshold;
determine a second calculated value, wherein the second calculated value is based on the kernel size;
determine a second difference by subtracting the second calculated value from the pixel intensity; and
classify the pixels that include a defect, wherein the second difference is above the threshold for the pixels that include a defect.

2. The system of claim 1, further comprising a bright field imaging system in electronic communication with the controller.

3. The system of claim 1, further comprising a dark field imaging system in electronic communication with the controller.

4. The system of claim 1, wherein the first calculated value is a moving mean.

5. The system of claim 1, wherein the second calculated value is a local median.

6. The system of claim 1, wherein the second calculated value is of each of the candidate pixels, and wherein the second difference is from each of the candidate pixels.

7. The system of claim 1, wherein the three dies are neighboring dies.

8. A method comprising:
receiving, at a controller, bright field images for three dies, wherein the three dies are on a transparent or translucent wafer, and wherein each of the bright field images includes a plurality of image rows and a plurality of image columns;

receiving, at the controller, dark field images for the three dies, wherein each of the dark field images includes a plurality of the image rows and a plurality of the image columns;

determining, using the controller, a first calculated value for each of the image columns of the bright field images and the dark field images, wherein the first calculated value is based on a kernel size applied along at least one of the image columns;

determining, using the controller, a first difference by subtracting the first calculated value from a pixel intensity in each pixel of the image columns;

classifying, using the controller, candidate pixels, wherein the first difference for the candidate pixels is above a threshold;

determining, using the controller, a second calculated value, wherein the second calculated value is based on the kernel size;

determining, using the controller, a second difference by subtracting the second calculated value from the pixel intensity; and classifying, using the controller, the pixels that include a defect, wherein the second difference is above the threshold for the pixels that include a defect.

9. The method of claim 8, wherein the first calculated value is a moving mean.

10. The method of claim 8, wherein the second calculated value is a local median.

11. The method of claim 8, wherein one of the first calculated value and the second calculated value is a fast Fourier transform with a low pass filter.

12. The method of claim 8, wherein one of the first calculated value and the second calculated value is a convolution with a Gaussian kernel.

13. The method of claim 8, wherein the second calculated value is of each of the candidate pixels, and wherein the second difference is from each of the candidate pixels.

14. The method of claim 8, wherein the pixel intensity is an average of three neighboring pixels in a same image column of the same die, wherein the second calculated value is an average of the candidate pixels and two neighboring pixels in the same image column of the same die, and wherein the second difference is based on the average of the candidate pixels.

15. The method of claim 8, wherein the first calculated value is determined for each of the bright field images and each of the dark field images.

16. The method of claim 8, wherein the first calculated value and the second calculated value are determined based on fused images of each of the bright field images and a corresponding one of each of the dark field images of a same die, and further comprising fusing each of the bright field images and the corresponding one of each of the dark field images to form the fused images.

17. The method of claim 16, wherein the second calculated value is a local median, and wherein the second calculated value and the second difference are determined based on both the bright field images and the dark field images, and wherein the threshold includes a bright field threshold and a dark field threshold.

18. The method of claim 16, wherein the second calculated value is a local median, wherein the threshold is for the fused images, wherein the classifying includes taking the square root of the product of a first value and a second value to form a third value and comparing the third value to the threshold, wherein the first value is the pixel intensity of the bright field image minus the local median of the bright field image, and wherein the second value is the pixel intensity of the dark field image minus the local median of the dark field image.

19. The method of claim 8, wherein the three dies are neighboring dies.

* * * * *